United States Patent [19]

Berlant

[11] Patent Number: 5,067,478

[45] Date of Patent: Nov. 26, 1991

[54] STRUCTURE AND METHOD OF MANUFACTURING AN ELECTRODE GLOVE FOR APPLYING ELECTRO-MASSAGE AND ELECTRO-ACUPRESSURE TO PATIENTS

[76] Inventor: Stephen R. Berlant, 392 Marple Rd., Broomall, Pa. 19008

[21] Appl. No.: 451,764

[22] Filed: Dec. 18, 1989

Related U.S. Application Data

[63] Continuation-in-part of Ser. No. 209,432, Jun. 21, 1988.

[51] Int. Cl.⁵ .............................................. A61H 1/00
[52] U.S. Cl. ................................ 128/24.5; 128/420.5; 128/783; 128/798; 128/800
[58] Field of Search ............... 128/800, 802, 788, 784, 128/795, 796, 798, 783, 420.5, 421, 24.1, 24.5, 62

[56]  References Cited

U.S. PATENT DOCUMENTS

| | | | |
|---|---|---|---|
| 206,474 | 7/1878 | Morel | 128/800 X |
| 1,545,413 | 7/1925 | Elmvall | 128/800 X |
| 3,845,771 | 11/1974 | Vise | 128/800 X |
| 4,207,904 | 6/1980 | Greene | 128/798 |
| 4,510,939 | 4/1985 | Brenman et al. | 128/800 X |

Primary Examiner—Edgar S. Burr
Assistant Examiner—Moshe I. Cohen

[57]  ABSTRACT

An electrode glove with a flexible, elastomeric, electrically-insulating shell, an optional moisture absorbant fabric liner, and a single, flexible, elastomeric, easily-cleaned or disposable, electro-chemically inert electrode is described for applying TENS and massage or acupressure to patients. In the preferred embodiment, the electrode glove is formed on a porcelain or metal hand-shaped form by coagulating a layer of conductive rubber over a layer of insulating rubber and attaching a connector, such as a carbon-rubber TENS electrode, to the conductive surface of the glove in the manufacturing process or prior to use by the clinician. In an alternate embodiment, the insulating and conductive layers are coagulated separately and a connector, such as a disposable electrocardiographic electrode, is affixed to the electrode glove so that the glove can be attached to a TENS unit, worn over the insulating glove, or any glove capable of insulating the hand against a TENS current, and removed for disposal after use.

14 Claims, 1 Drawing Sheet

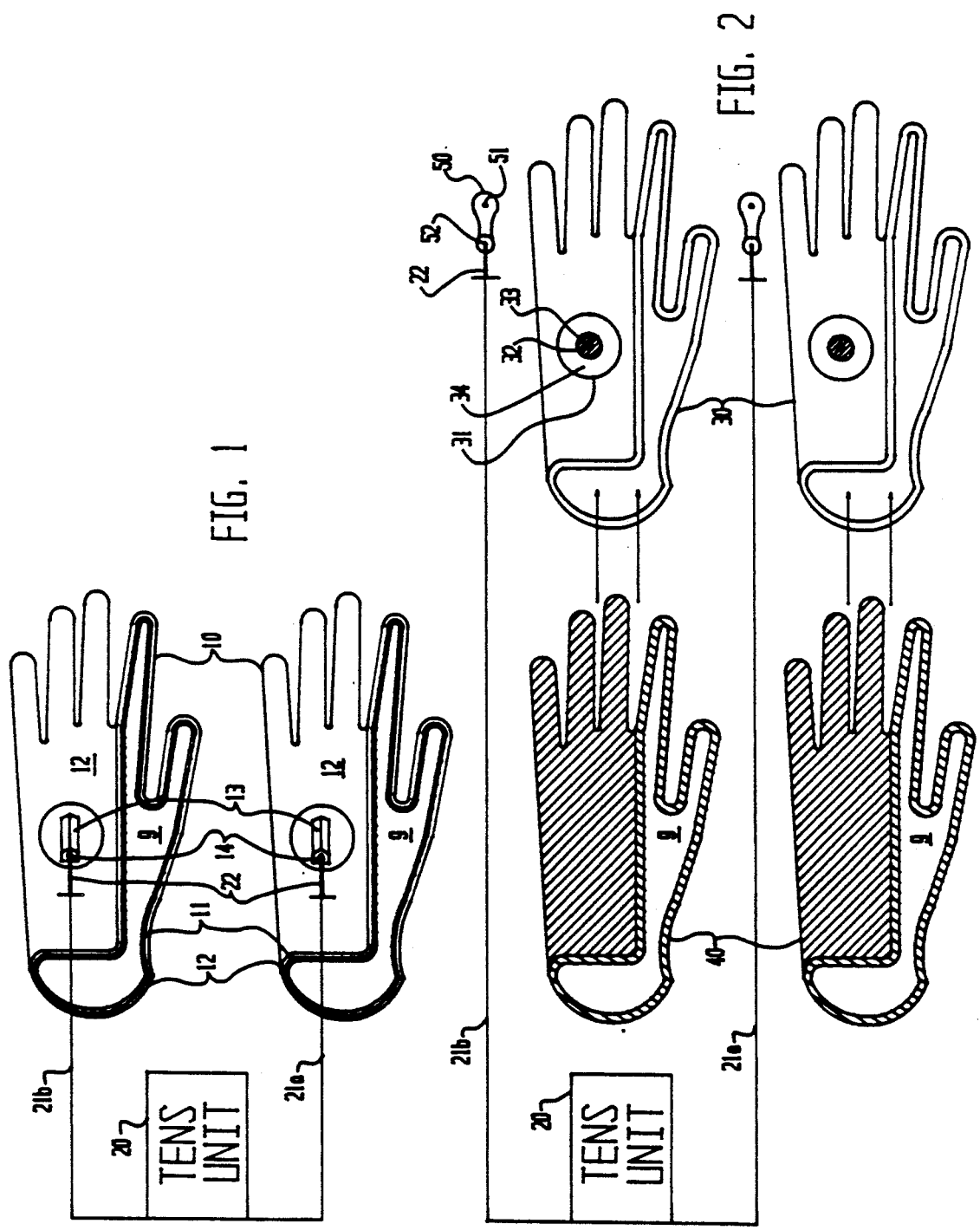

STRUCTURE AND METHOD OF MANUFACTURING AN ELECTRODE GLOVE FOR APPLYING ELECTRO-MASSAGE AND ELECTRO-ACUPRESSURE TO PATIENTS

This is a continuation-in-pat of Ser. No. 209,432, filed June 21, 1988, pending.

BACKGROUND OF THE INVENTION

This invention relates generally to the structure and method of manufacturing an apparatus for applying various forms of therapeutic "electro-touch" to a patient and more particularly to the structure of an electrode glove for use with a transcutaneous electrical nerve stimulation (TENS) unit for the purpose of applying a combination of TENS and whole-hand massage ("electro-massage") or acupressure ("electro-acupressure") to a patient.

Selective stimulation of relatively low-threshold, large, myelinated, afferent nerve fibers in a painful area can reduce pain by altering the pattern of neural input to the spinal cord. Although various methods exist for stimulating such fibers, three of the more commonly used methods are: (1) Transcutaneous electrical nerve stimulation (TENS), which involves attaching electrodes to the skin to deliver electrical energy to underlying nerves; (2) deep manual massage, which involves stimulating nerves through the application of differential pressure with the thenar and hypothenar eminence (the heel of the hand), the fleshy prominences on the palmar surface of the metacarpalphalangeal and phalangeal-phalangeal articulations (the palm side of the knuckle joints), and the finger tips; and (3) acupressure (also commonly referred to as myotherapy or Shiatsu), which often involves applying more intense pressure to a specific trigger point, acupuncture point, or superficial point of a nerve with the tip of the thumb or the dorsal surface of a knuckle. Although different clinicians prefer to use various knuckles for this purpose, the most commonly used are those formed by the articulation of the proximal phalanges of the index and middle fingers with their respective metacarpal bones, and the articulations formed between the first and second phalanges of the same fingers.

Indeed, because it has been so well established that TENS and manual massage can both produce pain relief, but via different mechanisms, attempts have been made to allow a clinician to simultaneously apply both of these modalities with one electro-massage device. However, known devices are less than ideal for performing electro-massage, and none enable a clinician to also perform electro-acupressure, for reasons which can be understood by considering the following definitions and principles.

An electrode is technically an electric conductor through which a current enters or leaves a medium. (Lapedes, D.N., Dictionary of Scientific and Technical Terms. New York, McGraw-Hill), and the function of a biological electrode is specifically to "convert the electronic current flow that exists in the connecting metallic conductors in to an ionic current for passage through biological tissue." (Jodat, R.W., Larson, S.J., Sances, A.. Neural Assist Devices. In Cook, A.M., Webster, J.G. (eds.) Therapeutic Medical Devices. Englewood Cliffs, N.J., 1982, p.127). More specifically, a TENS electrode, such as that on an electro-touch glove, functions to drive ions of a biologically compatible coupling agent, which is used to overcome the skin's high impedance, through the skin to excite underlying nerves. However, this must be done without driving ions of the electrode material itself onto and/or through the skin, because chronic exposure to such ions can cause severe skin reactions. In accord with these principles, and the well known principle that skin resistance decreases and current penetration increases as the size and distance between TENS electrodes increases, electro-massage should ideally be performed using the palms and fingers of two well-separated hands and electro-acupressure using the thumbs and/or dorsal surface of one of the above knuckles, with the hands and fingers covered entirely by an electro-chemically inert electrode material.

However, the devices disclosed by Elmvall, U.S. Pat. No 1,545,413, and Goy and Company, French Patent No. 456,865, do not have electrode material on the dorsal knuckles; and the devices disclosed in Fournier, French Patent No. 967,374, Morel, U.S. Pat. No. 206,674, Brenman, U.S. Pat. No. 4,510,939, and Shephard, U.S Pat. No. 3,556,105 do not have electrode material on the palm and heel of the hand or the dorsal knuckles. Further, the Fournier, Brenman, and Shephard devices have small point electrodes which increase currrent density, by concentrating it into a small electrode area, to the extent that punctate skin burns can be produced by the intensity of current that is often required for electro-massage. Thus, such electrodes are commonly used only to detect or apply the relatively low intensity current that is needed to diagnose pathology in various organs. In fact, the glove described in Brenman has anodal and cathodal point electrodes in close proximity, because it was specifically designed so that one hand could be used to focus low intensity current on the prostate gland or anal sphincter to diagnose disfunction. However, this short interpolar distance also renders the Brenman glove particularly less than ideal for electro-massage by facilitating the risk of electrical shorting across the conductive agent, which must be used for electromassage.

To overcome the problems associated with point electrodes, as well as the difficulty of attaching an appropriate electrode material to metallic conductors as discussed below, Elmvall taught connecting a plurality of metallic point electrodes together in a mesh which covered the palmar surface of a glove. However, metal is uncomfortable on the skin and is not electro-chemically inert, which allows the TENS current to carry metallic ions into the body. Also, the high resistance of the skin tends to convert the electricity in bare metal electrodes to heat, which can burn the skin. Thus, all other known electro-massage devices are covered by electrochemically-inert electrode materials. For example, the glove described by Goy and Company has leather over current conducting wires; the mittens described by Morel and Shephard and the glove described by Fournier have sponge over metal; and the mittens described by Lewin, U.S. Pat. No. 401,041, and Schnee, U.S. Pat. No 1,536,273, both have fabric over metal.

However, a fabric, sponge, or leather electrode must be wet to be conductive, and Schnee specifically claimed an absorbant electrode for his mitten, so that warm water could be used to give the patient "a warm electrical bath" [Page 1, Column 2, Line 102]. cut, wet electrodes, even when initially warm, can produce an uncomfortable clammy feeling and chills in the patient. Further, sponge and leather electrode materials have a short life expectancy; because, wet leather shrinks and hardens when it dries, and sponge eventually disintegrates when rubbed on the skin, as is required in electro-massage.

A fabric, sponge, or leather electrode just also be energized by an extensive network of metallic conducting materials - because the relatively high impedance of wet fabrics ponge, or leather, together with the limited voltage output of a TENS unit, prevent a single, small, metallic connector from distributing current over the entire surface of such as electrode. Further, to prevent migration and crimping of these materials during electro-massage, they must be attached to each other and the insulating liner in some way.

Obviously, extreme methods of making the above attachments would be unnecessary if metal conductors could also serve as electrodes, as Elmvall believed; or, if the above materials could simply be attached with, say, "sealing wax, or other suitable adhesive substance insoluble in water", as suggesed by Morel. (Page 2, Column 1, Line 1-2) But, the problems with elmvall's approach were discussed above, and Morel apparently failed to realize that: (1) his adhesive would also have to be conductive to allow current to pass from his metallic conductors to his sponge covering; and, (2) a conductive adhesive capable of bonding sponge to metal did not exist. Further, attaching the components of the referenced devices with glue was prohibited by the fact that: (1) the presence of wires between the fabric materials and the rubber liner in most devices would severely compromise any bond that could be formed by glue—especially because wires create hills and valleys int eh surfaces to be bonded and tend to migrate during electro-massage; (2) the promontories and depression of the hand would have made gluing a thin, hand shaped metallic electrode to a rubber liner extremely difficult, if not impossible; and, (3) such as method of attachment would have severely compromised a glove's flexibility, and/or caused the electrode to separate from the glove's liner sooner or later.

It appears that Elmvall did have knowledge of the difficulty of gluing ana electrode or metal to a rubber liner, because he connected his metallic palmer electrode to his rubber liner with "bent meal portions", vs glue. However, Elmvall's fasteners would produce current paths through a glove to the user's hand, and the integrity o a rubber liner is compromised by the holes created by any type of fastener, which causes the holes to expand into tears during use. Thicker rubber will obviously withstand fastening better than thinner rubber; but, the flexibility and sense of touch achieved while wearing such a glove would consequently be compromised.

The fact that other inventors simply ignored the problems associated with the necessity and difficulty of having to attach such materials to each other, or mistakenly assumed that such attachments would be easy to make, is evident from the fact that such inventors did not disclose methods of making the necessary attachments. For example, the patent for the electro-massage glove of Goy and Company, does not describe a method of securing the conducting wires to a rubber liner or leather electrode, or the electrode to the liner; and, the Schnee patent does not disclose a method for attaching Schnee's fabric electrode to his metallic mesh or his metallic mesh to his rubber liner. However, this arrangement, particularly in the Schnee mitten, would cause: (1) The electrode to continually slide off the metallic conductors, and/or the conductors to slide off the rubber liners, whenever the hand moved back and forth during electro-massage; and, (2) the electrode to make intermittent contact with the conductors as the pressures exerted by the hand on the device changed.

Indeed, the necessity and difficulty of having to attach such materials to each other is evident in the fact that most inventors did disclose rather elaborate ways of making such attachments, which appears to have been used as a basis for differentiating one device from another with respect to patentability. For example, Lewin suggested that his fabric electrode should have wires coursing in "small pockets housing metallic clamps or holders"; Shephard devised an elaborate scheme of tunnels, flanges, plates, and apertures, which were assembled with crimping, velcro, and heat sealing, to attach conductors to sponge electrodes; and Fournier taught an elaborate method of inserting conductors through his glove's liner and bringing them out again to attach to an electrode which screwed into a metallic housing.

It should also be noted that the above difficulties make it much harder to fashion the materials of an electro-massive device in to a true glove vs a mitten. Indeed, this fact can be invoked to explain why: (1) Lewin, Schnee, and Shephard, disclosed mitten structures for their electro-massage devices instead of gloves; (2) Morel suggested attaching sponge electrodes to the metallic conductors only on the palmar surface of a mitten, rather than over the entire surface of a true glove; and, (3) both Schnee and Morel discuss producing "gloves" while depicting mittens in their disclosures.

However, electro-massage mittens pack the fingers together in a way which prevents the therapist from rhythmically applying differential pressures with the individual fingers-tips, as is essential to applying electro-massage in the proper manner, or using the dorsal surface of a specific knuckle unrestrictedly to apply intense pressure to a particular point of the body, as is essential to applying electro-acupressure in the proper manner. In fact, the Morel and Shephard mittens are particularly unsuited for electro-acupressure, because neither has electrode material on its dorsal surface. Although the Lewin and Schnee mittens do have electrode material on their dorsal surfaces, the metallic conductors in the Lewin mitten are restricted to the mitten's palmar surface, which prohibits current from adequately energizing the dorsal surface of the electrically resistant fabric electrode. On the other hand, the metallic mesh in the Schnee mitten prevents flexing the mitten to form a fist and extending the dorsal surface of a specific knuckle to apply current only to a specific acupuncture-, trigger-, or nerve point. Also, mittens are more prone than gloves to slide off the hand during electro-massage.

In addition to the above problems, the rubber liners in the referenced devices tend to become hot and clammy, because they trap the perspiration which is emitted from the hand during electro-massage or electro-acupressure. A moisture absorbant liner could absorb such perspiration, as well as ease applying and removing the glove from the hand. However, the presence of such a liner adds another layer to the glove, which can compromise the sense of touch that the clinician can achieve during therapy. Thus, such a liner should ideally be optional in such a glove.

The referenced devices must also be taken out of service to be washed after every use, which is time consuming, and sponge and leather are not easy to clean. On the the hand, failure to thoroughly clean the electrode surfaces on any of the above devices is not hygienic, because using the same electrode on multiple patients can cross-contaminate their skins. Thus, patients today are concerned more than ever about using a device which has been used on another patient, and more and more medical devices are designed to be disposable.

The difficulty of cleaning any of the above electrodes could be eased by substituting a non-absorbant, carbon-rubber, TENS electrode (for example, Creene, U.S. Pat. No. 4,207,904; Larimore, U.S. Pat. No. 4,458,696) for the electrodes used in the referenced electro-massage devices. However, such a substitution is highly limited by a number of factors. For example, known carbon-rubber TENS electrodes provide relatively simple, flat, rectangular or circular stimulation surfaces, which are designed to be affixed to a particular location on a patient's body for extended periods of time with tape or adhesive. Thus, such electrodes are simple enough in structure that they can be manufactured by designing a mold and injecting molten carbon-rubber into it. But, no TENS patent discloses how to fashion such an electrode into the shape of a hand with an insulating liner, so that a clinician can hold it on the patient—because no reason exists for doing so with such electrodes.

Indeed, fashioning a carbon-rubber TENS electrode into the shape of a hand and substituting it for any of the electrodes in the referenced electro-massage devices would be prohibited by the same problems that confronted the earlier inventors—i.e., how to mechanically connect the electrode to each device's extensive network of metallic conducting materials, and/or one or both of these materials to an insulating liner. Although 1 investigated other materials and ways of making the necessary attachments, for example, attaching interlocking straps of velcro to both the electrode and the liner, all of these turned out to be as labor and/or material intensive as earlier methods.

Nor could the claimed glove be fabricated simply by substituting carbon rubber for the electrode material in prior devices via injection molding, because removing such electrodes for such a substitution exposes metallic conductors to which molten carbon rubber will not adhere. On the other hand, removing both the electrodes and the metal conductors in any of the prior devices would also remove the means of attaching the devices to a TENS unit, because the connectors in such devices were integrally connected to the conductors vs the electrodes themselves. Further, the carbon rubber could not be injection molded directly over the insulating rubber, because the latter would have to cure before the former was injected, and molten carbon-rubber will not adhere to cured rubber. For the same reason, molten carbon rubber cannot simply be applied to a cured rubber glove. Indeed, even if injection molding could be used to fabricate the claimed glove, a series of intricate hand shaped molds would be required to fashion different sized gloves, and such molds would be prohibitively complicated and expensive to make.

Electrically insulated rubber linesmens' gloves for use on electrical lines having voltages of 5-50 kV have been made by coagulating natural rubber latex on a porcelain or metal form. One method of making such a glove involves dipping a form in a tank containing a coagulating solution of, for example, calcium salts, consisting of 10% anhydrous calcium chloride, 10% calcium nitrate tetrahydrate, 20% acetone, and 60% alcohol, by dry weight; or, for example, a solution consisting of 10% acetic acid in methanol. 1-5% of this solution may consist of a parting agent, such as clay, bentonite, talc, mica, or diatomaceous earth, to ease the removal of the glove from the form.

The form is then withdrawn and air dried for 2-4 minutes as excess coagulant runs off. Following air drying, the form is immersed in a heated tank containing a solution of aqueous natural rubber latex. The form is then removed from the latex, the resulting rubber film is allowed to set, and the coagulant may be leached from the film with a water bath of up to 150 degrees F. for a period of 2-3 hours. The film is then cured by exposure to moderate heat (e.g., 150 degrees F.) and removed from the form. The concentrations of the above substances and the above parameters can vary be substituted for depending conditions, temperature, . dwell time, desired glove thickness, etc., etc.

Another method of making linesmen's gloves invloves dipping the coagulant-coated form in a solution containing rubber in an organic solvent base, such as xylene. Although a glove made with this method resists moisture absorption, which compromises electrical resistance, better than a glove made with aqaueous latex, solvent dipping requires more dips than the aqueous process and is, thus, more expensive. However, because the claimed glove must only insulate against currents of less than 500 V with total charges in the microcoulomb range, the aqueous dipping process is sufficient to provide the required electrical resistance even when the glove is submerged in water.

Other rubber gloves are also "supported" by fitting a flexible moisture absorbant fabric over the form and coating the fabric with coagulant. In this case, it is important to prevent the latex from penetrating or "striking-through" the fabric by adjusting the dipping time and depth of penetration of the form or sizing the fabric.

Some rubber gloves are also "overdipped" with special rubber compounds designed to improve heat, puncture, or chemical resistance, as, for example, is the glove patented by Hart and Collier, U.S. Pat. No. 4,218,779. In the overdipping process, the form containing the rubber film is removed from the heated tank of latex as described above. Instead of leaching the coagulant, however, the form is rotated in air, to facilitate the setting of the rubber film, and then dipped in the overdip compound. The form may be redipped in coagulant and/or the overdip compound a number of times until the desired thickness is achieved. The glove is then processed further, as described above.

Although overdipping is not uncommon, I am not aware that any electrically insulated glove has ever been overdipped in any compound. In fact, it would be radically opposed to the intended purpose of such a glove to overdip it in an electrically conductive compound and attach an electrical connector for the purpose of passing current across the glove's surface. Nor am I aware that any rubber glove has ever been overdipped with an electrically conductive compound and/or had an electrical connector attached to it.

Other rubber gloves have been rendered electrically conductive to bleed static electricity from the hands of workers that perform, for example, electronic manufacturing tasks or handle explosives. However, the electrical resistance between any two points on the exterior surface of such gloves typically measures $1 \times 10^6$ ohms, which is three orders of magnitude above the $1 \times 10^3$ ohms needed for a glove to transmit electricity from a connector attached to a TENS unit over the glove's exterior surface to a patient's body. Further, such anti-static gloves have never been designed with or to be used over an electrically insulating liner, since static electricity could not shock the hand. Nor have anti-static gloves ever been equipped with or to accept an electrical connector for other purpose of attaching the glove to a TENS unit, since such gloves cannot transmit a TENS current over their surfaces.

SUMMARY OF THE INVENTION

It is a principle object of this invention to provide an electrode glove which allows the user to apply electro-massage or electro-acupressure with the palms and individual fingers of two well separated hands and/or the dorsal surfaces of individual knuckles.

Additional objects of this invention are to avoid: 1) the high current densities caused by point electrodes; (2) the potential for electrical shorting caused by having anodal and cathodal point electrodes on fingers of the same glove; (3) the potential for passing metallic ions into he skin; (4) the difficulty of cleaning moisture absorbant electrodes; (5) the inability to sue the dorsal surfaces of knuckles to apply electro-acupressure; (6) the tendency of a mitten to pack he fingers together and prevent the use of individual fingers; (7) the need to and difficulty of using mechanical or chemical means to attach metallic conductors, an insulating liner, and an electrode to each other; (8) the need to energize the electrode with a connector attached to underlying metallic conductors; (9)f the high cost associated with the need to attach such a connector to the glove; (10) the high start-up cost of developing complex and expensive injection molds used to manufacture TENS electrodes; and (11) the tendency of prior rubber-lined electrode gloves to become hot and clammy by trapping perspiration on the hand.

The above and over objects are realized in a flexible, electrically-insulated glove having individual fingers, a single, easily cleared or disposable electrochemically-inert electrode that will not migrate during use, and, optionally, a moisture absorbant liner. The electrode glove can be fabricated relatively inexpensively and with low start-up costs by coagulating natural rubber latex on a hand-shaped metal or porcelain form, or on a form that has been fitted with a moisture absorbant fabric, to form the electrically-insulating shell, and co-agulating carbon-rubber latex over the insulating shell to form the electrode. In an alternate embodiment, the insulating shell and electrode can be coagulated independently as separate gloves, the shell applied to the hand of the clinician, and the electrode glove applied over the insulating shell. A carbon-rubber TENS or an electrocardiograph electrode can be affixed and electrically coupled to the exterior surface of the electrode glove in either embodiment to serve as a connector for the TENS unit as part of the fabrication process or by the clinician prior to use.

DESCRIPTION OF THE DRAWINGS

FIG. 1 is a cross-sectional view of a pair of integrated insulated-electrode gloves with pin connectors and apparatus therewith to apply electro-massage and electro-acupressure according to the invention.

FIG. 2 is a side view of a pair of disposable electrode gloves with snap connectors, a pair of insulating gloves, indicating the manner of applying the electrode gloves over the insulating gloves and apparatus therewith to apply electro-massage and electro-acupressure according to the invention.

FIG. 1 shows a pair of integrated insulated-electrode gloves 10 according to the invention. Each glove 10 includes a shell 11 formed of an electrically-insulating, flexible, elastomeric material, such as natural rubber, approximately 30 mils thick, which may be lined with a flexible, moisture absorbant fabric 9, such as cotton. The entire shell is covered by a layer of electrically-conductive, flexible, elastomeric material, such as carbonized-rubber, about 5 mils thick, which constitutes an electrode 12. A carbon-rubber connector 13 including one or more small holes 14 formed to accept the pins 22 on the lead wires 21a, 21b of a TENS unit 20 is attached to the exterior surface of the electrode glove 10 over the dorsal hand with adhesive The integrated insulated-electrode glove 10 is fabricated by coagulating the insulating rubber shell 11 directly on a porcelain or metal form or over a form that is first fitted with the moisture absorbant fabric liner 9. Before the shell 11 is allowed to cure, the hand-section of the shell is overdipped with natural rubber which has been loaded with enough carbon-black to yield an electrode 12 with a resistance of approximately 1000 ohms across any two surface points. The integrated insulated electrode glove 10 is then cured and removed from the form. The connector 13 may be applied to the dorsal surface of the glove 10 with adhesive or tape in the manufacturing process or by the clinician prior to use.

The TENS unit 20 is a small, portable, battery operated device which emits monophasic direct current or biphasic pulses having zero net direct current. The amplitudes of the pulses are typically up to 60 milliamps with durations of up to 500 microseconds and pulse rates of up to 200 hertz. The current emitted by TENS units which are powered by higher voltages, for example, 220 V AC, can be much greater than those previously described. For example, one type of AC powered TENS unit known as high voltage pulsed galvanic stimulator (HVPGS), is capable of emitting pulses of up to 500 volts. Another type of TENS unit known as the Russian Faradic Unit, can emit pulses at rates of up to 2000 hertz. A special class of TENS unit known as a Functional Electrical Stimulation (FES) unit, is a battery operated unit which is specifically designed to elicit timed cyclical contractions to strengthen muscles or prevent atrophy from disuse.

In operation, and as shown in FIG. 1, an integrated insulated-electrode glove 10 is worn on one hand. The pin 22 on the distal end of one lead wire 21a of the TENS unit 20 is inserted into the hole 14 in the connector 13. The pin 22 on the distal end of the other lead wire 21b of the TENS unit 20 is connected to the integrated insulated-electrode glove on the other hand.

In an alternate embodiment, as shown in FIG. 2, the insulating shell 40 and the electrode 30 are coagulated as separate gloves, allowing the electrode glove 30 to be removed and disposed of. A connector 31 with a sponge center 32 which is impregnated with an electro-conductive gel is connected to the electrode glove. Protruding from the sponge center 32 of the connector 31 is a male snap 33 formed to insert into the spring-loaded receptacle 51 on the bottom of the female snap adapter 50. On the proximal end of the female adapter 50 is a hole 52 to accept the pin 22 on the distal end of the lead wire 21a of the TENS unit 20. The sponge center 32 of the snap connector 31 is surrounded by a porous mesh tape 32 for attaching the connector to the exterior surface of the electrode glove 30.

The electrically insulated glove 40 may be coagulated specially for the purpose of being worn under the electrode glove 30, or it may be an electrical lineman's glove, which has been expressly designed and tested for use on high voltage electrical lines. In either case, an 11.5 inch long glove consisting of water-based latex must be approximately 30 mils thick to prevent detectable currents from passing through the glove when the glove is immersed in 7.5 inches of water and subjected to 500 V of 60 Hz AC, in accord with the American Society for Testing and Measurement's Proof Test Standards (D-120 -84a) for rubber insulating gloves.

In operation and as shown in FIG. 2, one electrode glove 30 is applied and worn over an electrically insulated glove 40. The pin 22 on the end of one lead wire 21a from the TENS unit 20 is inserted into the hole 52 on the female snap adapter 50. The male snap 33 on the connector 31 of the electrode glove 30 is inserted into the receptacle 51 on the bottom surface of the female snap adapter 50. The pin 22 on the end of the other lead wire 21b of the TENS unit 20 is connected in the same way to another electrode glove 30 which is worn on the other hand over an electrically insulating glove 40. An electrically conductive lotion, gel, or warm water is applied to the area of the patient to be treated and the gloves placed flat on that area. The TENS unit is turned on and the current intensity slowly increased until the desired effect is created. In another operative mode, one electrode glove 10 or 30 may be connected to one lead of a TENS unit and be other lead may be connected to a dispersive electrode, which is placed on the patient.

Some of the many features and advantages of the present invention are now apparent in view of the foregoing discussion. For example, an electrode glove having an electro-chemically inert, easily-cleaned or disposable electrode which covers substantially the entire palmar and dorsal surface of the hand and individual fingers has been described. The integrated-insulated embodiment of this electrode glove is formed by coagulating an electrically conductive elastomer, such as carbonized-rubber, over an electrically-insulating elastomeric shell of, for example, natural rubber, which has been coagulated directly on a coagulant-coated porcelain or metal ferm, or on a form that has first been fitted with a moisture absorbant fabric coated with coagulant. The disposable electrode glove is formed by coagulating the insulating liner and electrode glove separately and wearing the latter over the former. A TENS or electrocardiograph electrode is affixed and electrically coupled to the exterior dorsal surface of either embodiment as part of the manufacturing process but may be affixed by the clinician prior to use. When applying electro-massage, the stimulating electrodes can be significantly separated from each other to permit maximum current penetration of tissue and prevent shorting between the electrodes; while the substantial electrode surface provided by the invention minimizes the high current density which can result from small point electrodes. The manufacturing process has a low start-up cost because it uses readily-available hand-shaped forms used to make other rubber gloves.

It will be recognized by those skilled in the art that changes or modifications may be made to the above described embodiments without departing from the broad inventive concepts of the invention. It is understood therefore that the invention is not limited to the particular embodiments which are described, but is intended to cover all modifications and changes within the scope and spirit of the invention as defined in the appended claims.

What is claimed is:

1. Apparatus for applying electro-massage and electro-acupressure for use with a sauce of pulsed electrical energy such as a TENS unit, said apparatus comprising:
   a glove covering substantially al of the fingers, palm and dorsal surfaces of a hand, said glove being formed of a flexible, electrically-insulating layer of material capable of insulating the hand against pulsed, direct currents at voltages of up to 500 volts;
   an electrode affixed to an covering substantially all of the exterior surface of said glove, said electrode being formed of a non-metallic, flexible, electrically-conductive layer of material deposited as a coating.

2. Apparatus as recited in claim 1 further comprising a connector means for attaching to the lead wire from a TENS unit disposed on said electrode 3. Apparatus as recited in claim 1 further comprising a flexible, moisture absorbant fabric lining he interior surface of said electrically insulating layer.

4. Apparatus as recited in claim 1 wherein said electrode has been deposited as a coating by the process of coagulation.

5. Apparatus as recited in claim 1 wherein said electrode has been deposited as a coating by he process of dipping.

6. Apparatus as recited in claim 1 wherein said electrode has been deposited as a coating on the insulating layer so as to e integrally formed therewith.

7. Apparatus as recited in claim 1 wherein said electrode is formed of an elastic material.

8. Apparatus for applying electro-massage and electro-acupressure for use with a source of pulsed electrical energy, such as a TENS unit, said apparatus comprising:
   an electrode glove constructed to cover substantially al of the fingers, palmar, and dorsal surface of a hand, said electrode glove being formed of a flexible, electrical conductive, non-metallic material; and,
   an insulating liner glove constructed to cover substantially all of he fingers, palm, and dorsal surface of a hand and to be worn over the hand and under said electrode glove, said insulating liner glove being formed of a flexible, electrically insulating material capable of insulating the hand against pulsed direct currents at voltages of up to 500 volts.

9. Apparatus as recited in claim 8 wherein said electrode glove is formed by the process of dipping.

10. Apparatus as recited in claim 8 wherein said electrode glove is formed by he process of coagulation.

11. Apparatus as recited in claim 8 wherein said electrode gone is formed of an elastic material.

12. Apparatus for applying electro-massage and electro-acupressure for use with a source of pulsed electrical energy , such as a TENS unit, said apparatus comprising:
   an electrode glove constructed to cover substantially all of the fingers, palmar, and dorsal surface of a hand, said electrode glove being formed of material consisting of a flexible, electrically conductive, non-metallic, elastic material; and, a connector means for attaching to the lead wire from said source of pulsed electrical energy.

13. Apparatus of applying electro-massage and electro-acupressure for use with a source of pulsed electrical energy, such as a TENS unit, said apparatus comprising:

an electrode glove constructed to cover substantially all of the fingers, palmar, and dorsal surface of a hand, said electrode glove being formed of a flexible, electrically conductive, non-metallic material, said material being the product of a dipping operation; and, a connector means for attaching to the lead wire from said source of pulsed electrical energy.

14. Apparatus for applying electro-massage and electro-acupressure for use with a sauce of pulsed electrical energy, such as a TENS unit, said apparatus composing:

an electrode glove constructed to cover substantially all of the fingers, palmar, and dorsal surface of a hand, said electrode glove being formed of a flexible, electrically conducive, non-metallic material, said material being the product of a coagulation operation; and, connector means for attaching to the lead wire from said source of pulsed electrical energy.

* * * * *